US010466324B2

(12) United States Patent
Grodzki

(10) Patent No.: US 10,466,324 B2
(45) Date of Patent: Nov. 5, 2019

(54) METHOD AND MAGNETIC RESONANCE APPARATUS DETERMINING MARKINGS ON A QUANTITATIVE IMAGE DATA

(71) Applicant: Siemens Healthcare GmbH, Erlangen (DE)

(72) Inventor: David Grodzki, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 76 days.

(21) Appl. No.: 15/898,553

(22) Filed: Feb. 17, 2018

(65) Prior Publication Data

US 2018/0238982 A1 Aug. 23, 2018

(30) Foreign Application Priority Data

Feb. 17, 2017 (DE) ........................ 10 2017 202 601

(51) Int. Cl.
*G01R 33/483* (2006.01)
*A61B 5/055* (2006.01)
*G01R 33/3415* (2006.01)
*G01R 33/54* (2006.01)
*G01R 33/50* (2006.01)

(52) U.S. Cl.
CPC .......... *G01R 33/4833* (2013.01); *A61B 5/055* (2013.01); *G01R 33/3415* (2013.01); *G01R 33/543* (2013.01); *G01R 33/50* (2013.01)

(58) Field of Classification Search
CPC .............. G01R 33/4833; G01R 33/543; G01R 33/3415; G01R 33/50; A61B 5/055
See application file for complete search history.

(56) References Cited

U.S. PATENT DOCUMENTS

2012/0093385 A1* 4/2012 Yokosawa ............ A61B 5/0037 382/131
2016/0155238 A1* 6/2016 Bachschmidt ............ G06T 7/11 382/131
2016/0292859 A1 10/2016 Magda et al.
2017/0315200 A1 11/2017 Kiefer et al.

* cited by examiner

*Primary Examiner* — G. M. A Hyder
(74) *Attorney, Agent, or Firm* — Schiff Hardin LLP

(57) ABSTRACT

In a method and apparatus for automatically determining a slice position in a magnetic resonance (MR) system, for acquiring at least one MR image of an anatomical structure in an object undergoing examination; at least one MR overview data set of the object undergoing examination, which contains the anatomical structure, is acquired. Furthermore, quantitative MR overview data of the object undergoing examination are determined in which, for at least some image points of the MR overview data set, a physical variable of the object undergoing examination is determined quantitatively and with spatial resolution. Further, in the quantitative MR overview data, at least one marking is ascertained using the physical variable and previously stored reference data in which the value of the physical variable is specified in dependence on a basic field strength of the MR apparatus and for at least two different basic field strengths, and the slice position is determined using the ascertained marking.

10 Claims, 3 Drawing Sheets

| Anatomy | Size | Field strength 0.5T 1.5T 3T 7T |
|---|---|---|
| Cruciate ligament | T1 T2 | |
| Eye | T1 T2 | |
| | | |

10
11
13
12
20
HF control unit
14
15
Gradient control unit
Image sequence controller
16
17
Input unit
Display unit
18
19
Processor unit
Memory unit
21

26

| Anatomy | Size | Field strength 0.5T 1.5T 3T 7T |
| --- | --- | --- |
| Cruciate ligament | T1 T2 | |
| Eye | T1 T2 | |
| | | |

METHOD AND MAGNETIC RESONANCE APPARATUS DETERMINING MARKINGS ON A QUANTITATIVE IMAGE DATA

BACKGROUND OF THE INVENTION

Field of the Invention

The present invention concerns a method for automatically determining a slice position in a magnetic resonance (MR) system, and to an MR system and an electronically readable data storage medium for implementing such a method.

Description of the Prior Art

In contrast to other medical slice imaging modalities such as computed tomography, in magnetic resonance tomographic imaging it is possible to generate slice images of an object undergoing examination in any desired orientation.

However, these almost infinite possibilities for adjustment present a high potential for error, and can result in poor reproducibility of image results. This is particularly the case if an inexperienced user of the MR system makes an incorrect selection for orientation and thereby causes a pathology to be missed. It is thus highly important that the orientation of a slice position for a diagnostic task or for a particular examination region, such as the head, knee or spinal column, should follow certain standards and that the user should make the correct choice of slice position for a diagnostic task or examination region. The person operating the MR system can orient himself or herself using distinctive anatomical structure such as the eyes or cruciate ligament. The correct choice of slice position is important both for adjustments during the image acquisition itself and for the choice and position of pre-pulses, such as saturation pulses.

To make it as easy as possible for the technician to operate the MR system, and to keep the error rate as low as possible, so-called “auto-align” methods have been developed, which can automatically suggest an advantageous slice position with the aid of pattern and landmark recognition. In a manner similar to that when a human operates the device, the algorithm used for this recognizes markings, also called landmarks, in the image. These may contain distinctive anatomies, sudden changes in contrast, or a combination thereof. In an additional training method, the algorithm may be further improved using training data sets from real patients.

Among other things, the image contrast is of crucial importance in this context. For example, if the anatomy used for marking appears dark in the image data set that is used as the basis for performing the auto-align method, while the algorithm searches for bright intensities, then the algorithm will fail. It is thus an objective of algorithms of this kind to establish both acquisition of the image data set—called the MR overview data below—that is used as the basis for performing the automatic determination of the slice position, and recognition so that such algorithms function with a high hit rate for a broad base of patients and for the various field strengths of the main magnetic field.

Recently in clinic MR systems, higher field strengths such as 7 T are gaining in importance. Moreover, there are still a large number of low-field systems, with field strengths of <0.5 T. Because relaxation times of nuclear spins vary with field strength, it may at times be difficult to generate the required contrast in the MR overview data over a reasonable measuring time or with good quality. In this case, it may be necessary to adapt the algorithm to determine the slice position automatically.

SUMMARY OF THE INVENTION

An object of the invention is to improve methods for automatically determining slice positions such that, with different MR systems, they recognize the desired anatomy with a high degree of reliability, and thus correctly suggest the slice position with a high likelihood of a hit.

A method is provided for automatically determining a slice position in an MR system for capturing at least one MR image of an anatomical structure in an object undergoing examination. In one step of the method, at least one MR overview data set of the object undergoing examination, which contains the anatomical structure, is acquired. Furthermore, in a computer, quantitative MR overview data of the object undergoing examination are determined in which, for at least some image points of the MR overview data set, a physical variable of the object undergoing examination is determined quantitatively and with spatial resolution. In the quantitative MR overview data, at least one marking is ascertained using the physical variable and previously stored reference data. In the reference data, the value of the physical variable is specified in dependence on a basic field strength of the MR system and for at least two different basic field strengths. Then, the slice position is determined in the computer using the ascertained marking. An electronic signal representing the determined slice position is made available from the computer.

When a slice position is automatically determined according to the invention by the MR system, the determination of the slice position is based not on a relative contrast behavior or on signal intensity values that have been measured directly, but on quantitative values, specifically quantitative values of the physical variable, which can be calculated with the use of MR images. The physical variable that is determined can include, for example, a T1 time, a T2 time, a T2* time or a so-called “off resonance” or frequency shift. Moreover, since reference data that contains the quantitative value of the physical variable for different basic field strengths is used, it is possible to apply the described method with different MR systems, without time-consuming adaptation to the individual MR system. This means that the inventive method can be used with different MR systems of different basic field strengths and still enables a high hit rate without major adaptation. The use of the values of the physical variable also makes the method less dependent on a contrast behavior that is highly dependent on the imaging sequence on the basis of which the anatomical structures required for automatically determining the slice position are identified.

The reference data may be used, for example, to determine the value of the physical variable at the basic field strength present in the MR system, wherein the marking is determined in the quantitative MR overview data taking into account the determined value of the physical variable. For example, if it is known that a certain anatomical structure, such as a cruciate ligament or a patient’s eyes, has a particular T1 time, then quantitative MR overview data, so-called T1 cards, can be created in which the T1 times of the objects presented are coded in grayscale values or color values. This then makes it possible to identify the desired anatomy with a high hit rate by searching for the tissue with the desired T1 time.

It is further possible, using the marking that was determined from the quantitative MR overview data, to determine the slice position of a number of slices that are either parallel to one another or are at a defined location in relation to one another.

The marking can also serve to determine not the slice position itself for generating the MR image, but the slice position in which magnetization is to be prepared by irradiation with HF pulses.

For ascertaining the marking, it is also possible to determine a tissue type in the object undergoing examination using the physical variable, wherein the slice position is determined using the recognized tissue type. Here, the reference data store the value of the physical variable for a number of tissue types. Possible tissue types are, for example, ligaments, such as the cruciate ligament, or other readily identifiable tissues such as the eyes, vertebral body, or air interfaces.

The determination of the slice position can involve a tilt or rotation of the slice position in the object undergoing examination in relation to the coordinate system of the MR system. Since the slice images can be oriented in any desired manner, in particular the tilt of the slice, the precise location of the slice position in relation to the object undergoing examination is important for generating meaningful MR images.

It is possible for the reference data to have the value of the physical variable only for a different field strength compared to the basic field strength of the MR system being used. In this case, the reference data may represent a function that describes a relationship between the value of the physical variable and the basic field strength. This function can then be used to extrapolate the value of the physical variable for the basic field strength that is present. The inventive method thus can easily be transferred to other MR scanners with new field strengths.

The quantitative MR overview data may be determined as MR overview data generated using the magnetic resonance fingerprinting method. As well as the fingerprinting method, other methods for generating quantitative overview data are known. For example, T2 times may be determined in a multispin echo acquisition by the signal decay over the successive echoes. T1 times can be produced by adding inversion pulses with different inversion times.

Further, the invention concerns an MR apparatus that performs the inventive method, wherein the MR apparatus has a control computer and a memory and a scanner, wherein the memory stores control information that may be executed by the control computer so as to operate the scanner in order to implement the method.

The invention also encompasses an electronically readable data storage medium encoded with electronically readable control information (program code) that, when the storage medium is loaded in the control computer of the MR apparatus, cause the MR apparatus to perform the inventive method as explained above.

The features described above and below may be used not only in the combinations that are explicitly stated, but also in other combinations, unless explicitly indicated otherwise. Further, the various features described may be used individually.

DESCRIPTION OF THE PREFERRED EMBODIMENTS

Figure 1:
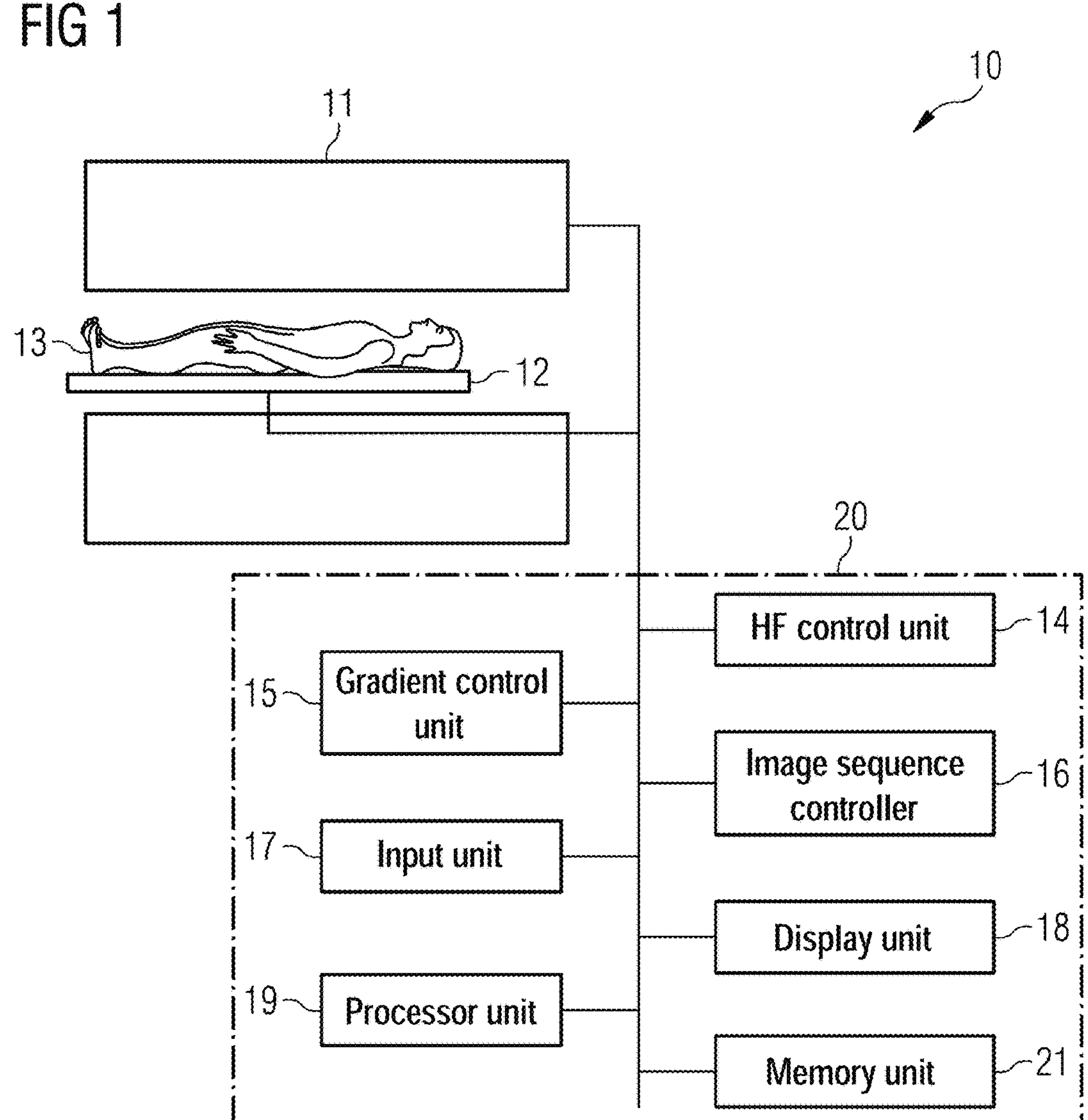
FIG. 1 schematically illustrates an MR system apparatus with which the method according to the invention can be performed.

The present invention will be explained in more detail below by preferred embodiments, with reference to the drawings.

In the figures, like reference numerals designate like or similar elements. Further, the figures represent schematic illustrations of different embodiments of the invention. The elements illustrated in the figures are not necessarily illustrated to scale, and are rather reproduced such that the function and purpose of the elements illustrated are understandable. The connections illustrated in the figures between functional units or other elements may also be implemented as an indirect connection, wherein a connection may be wireless or hard-wired. Functional units may be implemented as hardware, software or a combination of hardware and software.

With reference to FIG. 1, an MR apparatus is explained with which it is possible to improve automatic determination of the slice position. The MR apparatus 10 has an MR data acquisition scanner that has a magnet 11 for generating the polarization field B0 of a certain basic field strength. A person 13 undergoing examination, who is lying on a surface 12 is introduced into the magnet 11 (i.e. the scanner). For the purpose of capturing spatially encoded magnetic resonance signals there from the person 13 undergoing examination. The RF coils used for signal capture, such as a full-body coil or a plurality of local coils, are not illustrated for clarity. By introducing radiation using radio-frequency pulses and by switching magnetic field gradients, the magnetization generated by the polarization field B0 can be deflected out of the equilibrium position and be spatially encoded, and the resulting spin magnetization is deduced from the receiving coils, which are not shown. Those skilled in the art are entirely familiar with how MR images can be generated in an imaging sequence by the introduction of RF pulses and by switching magnetic field gradients in different combinations and sequences, so this need not be explained in more detail herein.

The MR apparatus 10 further has a control computer 20 that controls the MR apparatus 10. The control computer 20 has an RF controller 14 for controlling and generating the RF pulses for deflecting the magnetization. A gradient controller 15 is provided for controlling and switching the required magnetic field gradients. An image sequence controller 16 controls the sequence of magnetic field gradients and RF pulses, and hence indirectly the gradient controller 15 and the RF controller 14. A person operating the MR apparatus 10 can control the apparatus 10 via an input unit 17, and the MR images and other information required for control can be displayed on a display unit 18. A processor 19 may be provided for coordinated control of the different functional units that are provided in the control computer 20. For example, a memory 21 may have program modules or programs stored therein that, when they are executed by the processor unit, can control running of the MR system, as will be explained in detail below. Further, there may be stored in the memory unit 21 for example imaging sequences, and reference data in which the value of a physical variable such as the T1 time, T2 time or T2* time is stored in dependence on the basic field strength B0 of the MR system for different basic field strengths. As explained below, the program modules in the memory unit may help to determine a slice position automatically.

Figure 2:
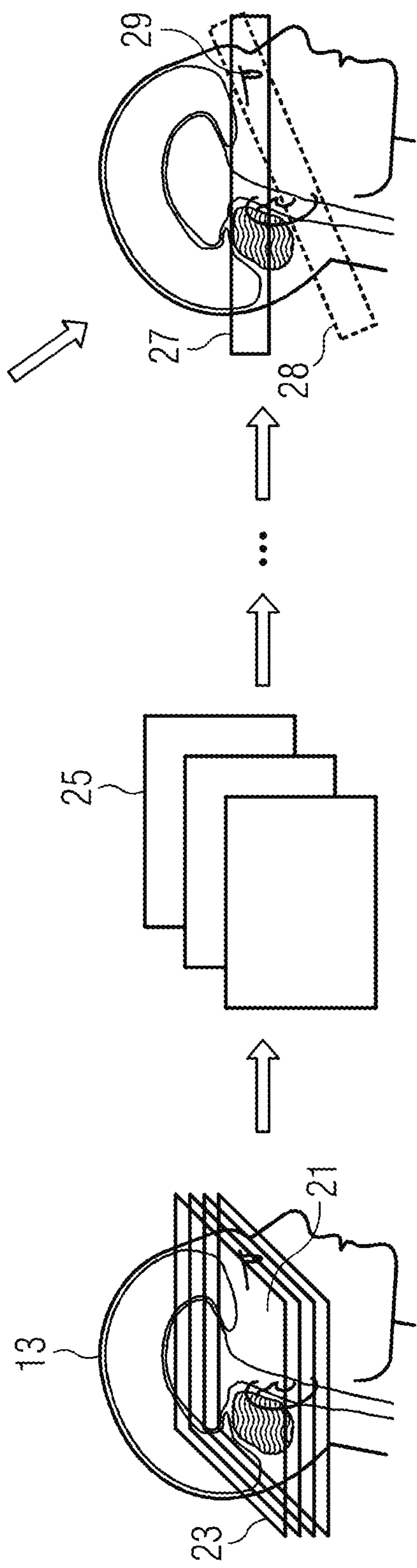
FIG. 2 schematically shows how, using an MR overview data set, quantitative MR overview data can be generated, with the use of which the slice position and a marking are then determined.

In conjunction with FIG. 2, it will be explained in general how the automatic determination of a slice position for capture of at least one MR image can be improved. An MR overview data set 23 of the object undergoing examination, in this case the person 13 undergoing examination, is captured. Here, this MR overview data set contains the desired anatomical structure from which a MR image will be generated later. In the example illustrated, this is the eyes 21. In a further step, a quantitative MR overview data set 25 is generated from the MR overview data set 23. This MR overview data set includes a physical variable of the object undergoing examination, quantitatively and spatially encoded, for at least some image points. The quantitative overview data may include, for example, quantitative values of the T1 time, the T2 time, the T2* time or the spin density.

To ascertain the quantitative image data, a method may be applied that includes the method of magnetic resonance fingerprinting, MR-F. For this, a pseudorandomized signal characteristic is applied to a magnetic resonance imaging method, the various materials or tissues having a unique signal development that simultaneously represents a function of the different material properties. Here, once the signal characteristic has been captured, pattern recognition is applied to the data and a quantitative depiction is generated. Once the quantitative image data has been obtained, it is possible to use reference data 26 to determine the value of the physical variable. The reference data 26 contain information on different anatomical structures and the associated physical variables, such as T1 time, T2 time, proton density and T2* time. These physical variables are stored in the reference data 26 for different field strengths, for example for the conventional field strengths between 0.5 T and 7 T. This reference data can then be used to determine the value of the physical variable for the desired anatomical structure and for the applicable basic field strength of the polarization field B0.

Once the value of the physical variable of the desired anatomical structure—such as the eye or a particular bone part—is known, the quantitative MR overview data 25 can then be examined to identify the marking 29—such as the eyes—that is needed for automatically determining a slice position for the capture of MR images and suggesting it to the person operating the device. In the example illustrated, this is for example a slice position 27 or a slice position 28, each of which runs through the identified marking—the eyes. The quantitative MR overview data helps to better identify anatomical structures in segmentation algorithms.

Figure 3:
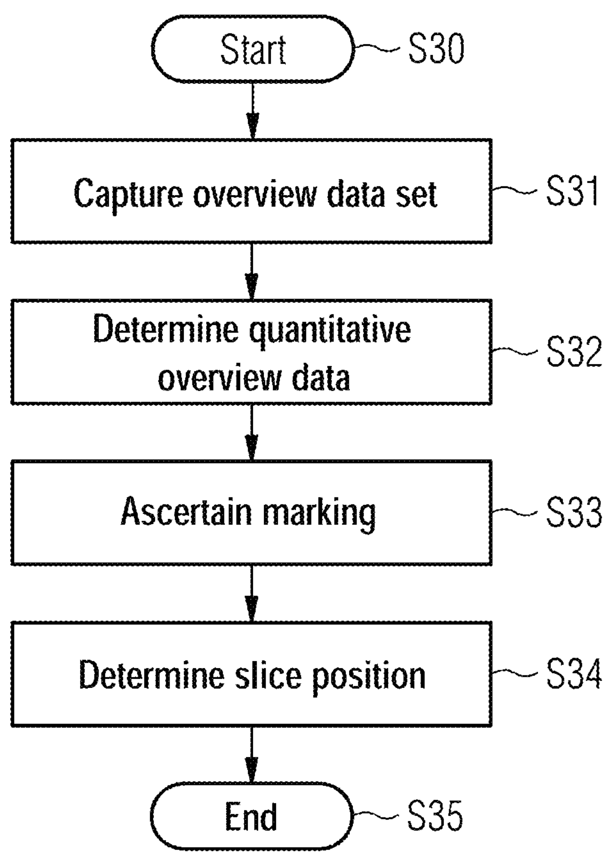
FIG. 3 is a flowchart of an embodiment of the inventive method for automatically determining a slice position with the use of quantitative MR data.

FIG. 3 summarizes the method. Once the method has started, in step S30, an overview data set is captured or determined, in step S31. This overview data set may for example be a low-resolution three-dimensional representation of the desired anatomical region. In a step S32, the quantitative overview data is then determined. The quantitative overview data may either be determined directly from the captured overview data, for example by the fingerprinting technique, or the overview data sets may be processed, for example to generate so-called T1 cards, wherein the characteristics of signal intensity in the MR overview data may be used to plot a T1 curve, and by means of this the T1 value in the corresponding image point and in the corresponding tissue can then be calculated. Similarly, T2 or T2-star cards of the object undergoing examination may be produced. Further, the method contains an item of information on the anatomical region in which an MR image generation is to be performed—for example the head or spinal column or knee. This may be done by selection by a person operating the device or by recognition of the anatomical structure in the overview data captured in step S31. Further, in order to locate a slice position, it is necessary to determine a distinctive anatomical structure. For example, certain bone corner shapes that any person under examination will have, or air inclusions in the paranasal sinuses, or the eyes, may be used as markings. Once the algorithm or the method has recognized the anatomical structure, then how a slice position or a plurality of slice positions must lie in order to be able to perform a particular clinical diagnostic task will also be known and defined. This marking is determined in the quantitative overview data, with the aid of the reference data 26 in FIG. 2. For different anatomical structures, the reference data contain different basic field strengths of the polarization field B0 and the quantitative values of the respective MR parameter represented in the quantitative MR overview data 25. Here, it is possible that the reference data does not contain any values in the reference data 26 for the basic field strength used. However, the reference data can represent a function describing a relationship between the physical variable and the field strength. If the value of the physical variable is now known for other field strengths and the basic field strength is entered, then the stored function can be used to extrapolate the value of the physical variable for the magnetic field used.

Referring once again to FIG. 3, this means that in the quantitative overview data, and using the reference data 26, the marking can be identified with spatial resolution, and on the basis of this marking the slice position is then determined in a step S34. Instead of abstract markings, the marking that is determined in step S33 may also comprise tissue types, such as the tissue type of the eye or of the cruciate ligament. Using the overview data 26, the associated value of the physical value can then be determined, wherein the image points having the identified value are then identified in the quantitative MR overview data. Once the marking is known in this way, the system can automatically determine a predetermined slice position in relation to the identified marking, and this is then the slice position at which the actual imaging is to be performed. In a step that is not shown, the imaging can then be carried out at the determined slice position. If the slice position is not the slice position for the final magnetic resonance imaging but a volume in which the magnetization is to be prepared by radiation with an RF pulse, then this may be performed in the step that is not shown, by radiation with one or more RF pulses for preparation of the magnetization.

The method ends at step S35. Using the method described above, it is possible to determine markings and slice positions automatically for further field strengths once the latter come onto the market. The quantitative values of the physical variable can either be measured or taken from the literature or indeed calculated using the function as explained above, and supplied to the reference data.

A method is thus provided by which the problem of dependence on field strength when automatically determining slice positions is solved in that the markings used are recognized from their quantitative properties and using a database of field-strength dependencies.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for automatically determining a slice position in a magnetic resonance (MR) apparatus in order to acquire at least one MR image of an anatomical structure of a subject, said method comprising;

operating said MR apparatus in order to acquire at least one MR overview data set of the examination subject, said MR overview data set containing said anatomical structure;

providing said at least MR overview data set to a computer and, in said computer, determining quantitative MR overview data from said at least one MR overview data set by, for at least some image points of said at least one MR overview data set, quantitatively determining a physical variable of the subject with spatial resolution;

from said computer, accessing stored reference data in which respective values of said physical variable are stored dependent on respective, different strengths of a basic magnetic field of the MR apparatus, for at least two different basic field strengths;

in said computer, ascertaining at least one marking in said quantitative MR overview data using said physical variable and the accessed referenced data; and in said computer, determining said slice position from said ascertained marking, and generating an electronic signal representing said slice position and making said electronic signal available from the computer.

2. A method as claimed in claim 1 comprising, in said computer, using said reference data to determine a value of the physical variable at a basic field strength that is currently present in said MR apparatus, and determining said marking in said quantitative MR overview data using the determined value of the physical variable.

3. A method as claimed in claim 1 comprising using said marking to ascertain a plurality of slice positions in said MR apparatus.

4. A method as claimed in claim 1 comprising using the ascertained marking to determine a slice position in the subject, which slice position in the subject is to be radiated with a radio frequency (RF) pulse emitted by said MR apparatus.

5. A method as claimed in claim 1 comprising ascertaining said marking by determining a tissue type in the subject using said physical variable, and determining said slice position using the determined tissue type, and wherein said reference data contains respective values of the physical variable for a plurality of different tissue types.

6. A method as claimed in claim 1 comprising determining said slice position by determining a tilt of the slice position in the subject relative to a coordinate system of the MR apparatus.

7. A method as claimed in claim 1 wherein said reference data contain a value of said physical variable for another basic field strength that differs from the basic field strength that is currently present in said MR apparatus, and wherein said reference data represent a function that describes a relationship between the value of the physical variable and the basic field strength.

8. A method as claimed in claim 1 comprising operating said MR apparatus to acquire said MR overview data set by executing an MR fingerprinting method.

9. A magnetic resonance (MR) apparatus comprising:

an MR data acquisition scanner;

a computer configured to operate said MR apparatus in order to acquire at least one MR overview data set of the examination subject, said MR overview data set containing said anatomical structure;

said computer being configured to determine quantitative MR overview data from said at least one MR overview data set by, for at least some image points of said at least one MR overview data set, quantitatively determining a physical variable of the subject with spatial resolution;

said computer being configured to access stored reference data in which respective values of said physical variable are stored dependent on respective, different strengths of a basic magnetic field of the MR apparatus, for at least two different basic field strengths;

said computer being configured to ascertain at least one marking in said quantitative MR overview data using said physical variable and the accessed referenced data; and said computer being configured to determine said slice position from said ascertained marking, and to generate an electronic signal representing said slice position and to make said electronic signal available from the computer.

10. A non-transitory, computer-readable data storage medium encoded with programming instructions, said storage medium being loaded into a computer system of a magnetic resonance (MR) apparatus, and said programming instructions causing said computer system to:

operate said MR apparatus in order to acquire at least one MR overview data set of the examination subject, said MR overview data set containing said anatomical structure;

determine quantitative MR overview data from said at least one MR overview data set by, for at least some image points of said at least one MR overview data set, quantitatively determining a physical variable of the subject with spatial resolution;

access stored reference data in which respective values of said physical variable are stored dependent on respective, different strengths of a basic magnetic field of the MR apparatus, for at least two different basic field strengths;

ascertain at least one marking in said quantitative MR overview data using said physical variable and the accessed referenced data; and determine said slice position from said ascertained marking, and generate an electronic signal representing said slice position and make said electronic signal available from the computer.

* * * * *